(12) United States Patent
Souza et al.

(10) Patent No.: US 10,183,024 B2
(45) Date of Patent: Jan. 22, 2019

(54) CRYSTALLINE FORMS OF IBRUTINIB

(71) Applicant: Apotex Inc., Toronto (CA)

(72) Inventors: Fabio E. S. Souza, Mississauga (CA); Annyt Bhattacharyya, Hamilton (CA); Bahareh Khalili, Brantford (CA); Allan W. Rey, Brantford (CA); Boris Gorin, Oakville (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 15/827,471

(22) Filed: Nov. 30, 2017

(65) Prior Publication Data

US 2018/0153895 A1    Jun. 7, 2018

Related U.S. Application Data (60) Provisional application No. 62/429,235, filed on Dec. 2, 2016, provisional application No. 62/453,166, filed on Feb. 1, 2017.

(51) Int. Cl.
| | | |
|---|---|---|
| *C07D 487/04* | (2006.01) | |
| *A61K 31/519* | (2006.01) | |
| *A61K 45/06* | (2006.01) | |

(52) U.S. Cl.
CPC ............ *A61K 31/519* (2013.01); *A61K 45/06* (2013.01); *C07D 487/04* (2013.01); *C07B 2200/13* (2013.01)

(58) Field of Classification Search
CPC ............................ A61K 31/519; C07D 487/04
USPC ........................................ 514/262.1; 544/262
See application file for complete search history.

(56) References Cited

U.S. PATENT DOCUMENTS

| | | |
|---|---|---|
| 9,409,911 B2 | 8/2016 | Honigberg et al. |
| 9,751,889 B2 | 9/2017 | Chen et al. |
| 9,828,383 B1 | 11/2017 | Purro et al. |
| 2017/0226108 A1 | 8/2017 | Adin et al. |
| 2017/0226114 A1 | 8/2017 | Cohen et al. |

FOREIGN PATENT DOCUMENTS

| | | |
|---|---|---|
| CN | 103923084 A | 7/2014 |
| CN | 105294696 A | 2/2016 |
| CN | 105646484 A | 6/2016 |
| CN | 105646498 A | 6/2016 |
| CN | 105646499 A | 6/2016 |
| CN | 106008529 A | 10/2016 |
| CN | 107286163 A | 10/2017 |
| EP | 3243824 A1 | 11/2017 |
| WO | 2008039218 A2 | 4/2008 |
| WO | 2013184572 A1 | 12/2013 |
| WO | 2015081180 A1 | 6/2015 |
| WO | 2015145415 A2 | 10/2015 |
| WO | 2016025720 A1 | 2/2016 |
| WO | 2016079216 A1 | 5/2016 |
| WO | 2016139588 A1 | 9/2016 |
| WO | 2016150349 A1 | 9/2016 |
| WO | 2016156127 A1 | 10/2016 |
| WO | 2016160598 A1 | 10/2016 |
| WO | 2016160604 A1 | 10/2016 |
| WO | 2016170545 A1 | 10/2016 |
| WO | 2017085628 A1 | 5/2017 |
| WO | 2017174044 A1 | 10/2017 |
| WO | 2018000250 A1 | 1/2018 |

OTHER PUBLICATIONS

Australian Public Assessment Report for ibrutinib; Australian Therapeutic Goods Administration; Mar. 2016; pp. 1-83.
Bernstein; Polymorphism in Molecular Crystals; Clarendon Press; Oxford; 2002; pp. 9-10.
CHMP assessment report (EMA/CHMP/645137/2014); European Medicines Agency; Jul. 24, 2014; pp. 1-140.
ICH Harmonised Tripartite Guideline; Impurities: Guideline for Residual Solvents Q3C(R5); 2011; pp. 1-29.
Zvonicek et al.; "First Crystal Structures of Pharmaceutical Ibrutinib: Systematic Solvate Screening and Characterization"; Cryst. Growth Des.; 2017; pp. 3116-3127; vol. 17.

*Primary Examiner* — Jeffrey H Murray
(74) *Attorney, Agent, or Firm* — The Webb Law Firm (57) ABSTRACT

The present invention provides crystalline forms of Ibrutinib. Specific crystalline forms provided by the present invention include Ibrutinib Form APO-I, an anhydrous form; APO-II, a methyl benzoate solvate of Ibrutinib; and APO-IV, a methyl salicylate solvate of Ibrutinib.

5 Claims, 8 Drawing Sheets

CRYSTALLINE FORMS OF IBRUTINIB

CROSS-REFERENCE TO RELATED APPLICATIONS

This application claims benefit of U.S. Provisional Patent Application Nos. 62/429,235 and 62/453,166, filed Dec. 2, 2016 and Feb. 1, 2017, respectively, the disclosures of which are hereby incorporated in their entirety by reference.

TECHNICAL FIELD

The present invention is directed to novel crystalline forms of Ibrutinib and processes for the preparation thereof.

BACKGROUND

The compound 1-[(3R)-3-[4-amino-3-(4-phenoxyphenyl)-1H-pyrazolo[3,4-d]pyrimidin-1-yl]-1-piperidinyl]-2-propen-1-one (1), commonly known as Ibrutinib, is described in WO 2008/039218 A2, for instance, in Example 1b. Ibrutinib is marketed in the United States as IMBRUVICA®, and is indicated for the treatment of patients with mantle cell lymphoma (MCL) who have received at least one prior therapy.

(1)

Crystalline forms of Ibrutinib are known, and have been disclosed, for example, in WO 2013/184572 A1, which reports non-solvated Ibrutinib Forms A, B and C, as well as solvated Forms D, E and F, formed with methyl isobutyl ketone, toluene and methanol, respectively. Further crystalline forms, including anhydrous, solvated and co-crystal forms are reported, for example, in WO 2015/081180 A1, WO 2015/145415 A2, CN 103923084 A, WO 2016/025720 A1, CN 105294696 A, CN 105646498 A, CN 105646499 A, CN105646484 A, WO 2016/079216 A1, WO 2016/139588 A1, CN 106008529 A, WO 2016/150349 A1, WO 2016/170545 A1, WO 2016/156127 A1, WO 2016/160598 A1 and WO 2016/160604 A1.

According to publicly available regulatory approval documents for Ibrutinib, such as the Australian Public Assessment Report (AusPAR), the drug substance Ibrutinib in the approved drug product IMBRUVICA®, is anhydrous Form A. This form of the drug substance is reported to exhibit pH dependent solubility, and to fall within Class II of the Biopharmaceutics Classification System (BCS). Class II drug substances have high permeability but low solubility, which can present a challenge to achieving good bioavailability. Other anhydrous forms of Ibrutinib, including Form B, are also reported to have low aqueous solubility. Known approaches to improving solubility and/or dissolution, and potentially the bioavailability, of a particular crystalline form of a Class II drug substance include, for example, particle size reduction techniques, formulation of the drug substance as the amorphous form, and formulation together with solubilizing excipients. According to the European CHMP Assessment Report (EMA/CHMP/645137/2014), the drug substance Ibrutinib in the approved drug product IMBRUVICA®, is subjected to micronization to facilitate dissolution in the drug product.

In some cases, the use of solvated forms of a drug substance can be useful in the development of a low solubility drug substance such as Ibrutinib since incorporation of a solvent molecule into the crystal lattice of a substance can directly alter the solubility and/or dissolution characteristics of the substance. Depending on the pharmaceutical acceptability and toxicity of the solvent, such a solvate form can be formulated to provide a drug product having enhanced dissolution and potentially improved bioavailability.

Additionally, solvated crystalline forms of Ibrutinib may be useful as intermediates in the provision of amorphous forms of Ibrutinib. Although amorphous forms of a drug substance typically exhibit more favourable solubility and/or dissolution characteristics than corresponding crystalline forms, achieving the high purity required for the bulk drug substance can be challenging when using amorphous forms owing to the nature of the processes typically employed for their preparation, such as spray drying, evaporation and lyophilisation. Unlike crystallization procedures, such preparative procedures do not allow for purification of the drug by separation of the drug from impurities that remain dissolved in the crystallization solvent. As a result, when employing these techniques for the preparation of amorphous forms, the purity of the input drug must equal or exceed the expected purity of the final bulk drug substance. When crystalline forms of a drug are not used as intermediates in the preparation of an amorphous drug substance, it is necessary to purify the drug by non-crystallographic techniques, which can complicate a commercial manufacturing process, or to conduct any necessary purification procedures on an earlier intermediate compound in the synthesis of the drug (with the further requirement that conversion of this intermediate to the drug does not result in the introduction of further impurities). In this way, crystalline solvate forms of Ibrutinib, which may be useful in the provision of amorphous forms of Ibrutinib, can contribute to the development of procedures for improving the dissolution properties of this drug substance.

Although solvates may be sought after, predicting the properties of an as yet undiscovered solvate form of a drug substance is currently not possible. Further, there is no way to predict whether a drug substance and solvent molecule will co-crystallize in the same crystal lattice, or the conditions under which co-crystallization will occur. Unlike the formation of salts, solvate formation is not aided by the formation of a strong ionic bond between acidic and basic moieties, but instead relies upon weaker non-ionic interactions.

Known solvated and hydrated crystalline forms of Ibrutinib are associated with various problems, such as reproducibility problems associated with the variable incorporation of water/solvent, low onset of dehydration of hydrated forms, the incorporation or use of toxic or questionable solvents for which no adequate safety data is available according to established ICH (International Council for Harmonisation of Technical Requirements for Pharmaceuticals for Human Use) guidelines such as Q3C(R5), or preparations that are impractical for commercial use. The tendency of forms to dehydrate limits their usefulness in commercial products since it requires specialized practices to avoid dehydration during drying, handling, storage and formulation activities. Furthermore, the variable and/or undefined nature of some of these forms has regulatory implications, as the characteristics of an active pharmaceutical ingredient must be well-defined and controlled.

Different crystalline forms of the same compound may have different packing, thermodynamic, spectroscopic, kinetic, surface and mechanical properties. For example, different crystalline forms may have different stability properties. A particular crystalline form may be more sensitive to heat, relative humidity (RH) and/or light. Alternatively or additionally, a particular crystalline form may provide more compressibility and/or density properties thereby providing more desirable characteristics for formulation and/or product manufacturing. Particular crystalline forms may also have different dissolution rates, thereby providing different pharmacokinetic parameters, which allow for specific forms to be used in order to achieve specific pharmacokinetic targets. Differences in stability may result from changes in chemical reactivity, such as differential oxidation. Such properties may provide for more suitable product qualities, such as a dosage form that is more resistant to discolouration when comprised of a specific crystalline form. Different physical properties of crystalline forms may also affect their processing. For example, a particular crystalline form may be more resistant to flow, or may be more difficult to filter and/or wash.

Although general approaches to crystalline form screening of active pharmaceutical ingredients are known, it is well established that the prediction of whether any given compound will exhibit polymorphism is not possible. Furthermore, prediction of the properties of any unknown crystalline forms, and how they will differ from other crystalline forms of the same compound, remains even more elusive (Joel Bernstein, *Polymorphism in Molecular Crystals*, Oxford University Press, New York, 2002, page 9).

Therefore, there exists a need for novel crystalline forms of Ibrutinib for use in providing improved drug products containing Ibrutinib and their manufacture.

SUMMARY

The Ibrutinib crystalline forms of the present invention exhibit differences in properties when compared to the known crystalline forms of Ibrutinib. Depending on the specific crystalline form of the invention used, properties that differ between the invention and known crystalline forms of Ibrutinib include: packing properties such as molar volume, density and hygroscopicity; thermodynamic properties such as melting and solubility; kinetic properties such as dissolution rate and chemical/polymorphic stability; surface properties such as crystal habit; or mechanical properties such as hardness, tensile strength, compactibility, tableting, handling, flow, and blending.

Additionally, the solvated crystalline forms of the present invention incorporate solvents included in the U.S. Food & Drug Administration's (FDA's) Generally Recognized As Safe (GRAS) list or Everything Added to Food in the United States (EAFUS) list. The GRAS list is an inventory of substances generally recognized by the FDA as having been adequately shown to be safe under the conditions of intended use. The EAFUS list contains ingredients added directly to food that the FDA has either approved as food additives, or has listed or affirmed as being GRAS. The solvated crystalline forms of the present invention are also highly stable, failing to desolvate even upon storage for 11 months in humid and high temperature conditions. The solvated crystalline forms of the present invention are well-defined and controllable as evidenced by single crystal X-ray diffraction (SCXRD) data. Furthermore, the crystalline forms of the present invention may be prepared by facile and industrially advantageous processes when compared to known crystalline forms of Ibrutinib in the art.

Differences in the properties of the crystalline forms of the present invention provide practical advantages that can be exploited to meet specific needs in the manufacture and formulation of Ibrutinib. For example, one or more solvated crystalline forms of the present invention use solvents and reagents which are more pharmaceutically acceptable and environmentally friendly than the solvents used to prepare some of the known forms of Ibrutinib.

Accordingly, in a first aspect of the present invention, there is provided a crystalline form of Ibrutinib, Form APO-I, characterized by a powder X-ray diffraction (PXRD) diffractogram comprising peaks, expressed in degrees 2θ (±0.2°), at 5.1°, 7.6° and 12.5°. In a preferred embodiment of the first aspect, the PXRD diffractogram further comprises at least three peaks, expressed in degrees 2θ (±0.2°), selected from the group consisting of: 10.1°, 11.1°, 14.2°, 15.4°, 16.3°, 17.3° and 18.7°. In a further preferred embodiment of the first aspect, the PXRD diffractogram further comprises peaks, expressed in degrees 2θ (±0.2°), at 10.1°, 11.1°, 14.2°, 15.4°, 16.3°, 17.3° and 18.7°.

In a second aspect of the present invention, there is provided a crystalline form of Ibrutinib, Form APO-II, that is a solvate of Ibrutinib and methyl benzoate. Preferably, in the solvate of the second aspect, the molar ratio of Ibrutinib to methyl benzoate is approximately 1:0.5. In a preferred embodiment of the second aspect, the solvate is characterized by a PXRD diffractogram comprising peaks, expressed in degrees 2θ (±0.2°), at 6.4°, 10.1° and 12.8°. In a further preferred embodiment of the second aspect, the PXRD diffractogram further comprises at least three peaks, expressed in degrees 2θ (±0.2°), selected from the group consisting of: 13.8°, 17.6°, 18.4°, 19.4°, 20.4°, 21.0°, 21.7°, 23.2°, 24.1° and 24.9°. In another further preferred embodiment of the second aspect, the PXRD diffractogram further comprises peaks, expressed in degrees 2θ (±0.2°), at 13.8°, 17.6°, 18.4°, 19.4°, 20.4°, 21.0°, 21.7°, 23.2 °, 24.1° and 24.9°.

In a third aspect of the present invention, there is provided a crystalline form of Ibrutinib, Form APO-IV, that is a solvate of Ibrutinib and methyl salicylate. Preferably, in the solvate of the fourth aspect, the molar ratio of Ibrutinib to methyl salicylate is approximately 1:0.5. In a preferred embodiment of the fourth aspect, the solvate is characterized by a PXRD diffractogram comprising peaks, expressed in degrees 2θ (±0.2°), at 6.4°, 10.1° and 12.8°. In a further preferred embodiment of the fourth aspect, the PXRD diffractogram further comprises at least three peaks, expressed in degrees 2θ (±0.2°), selected from the group consisting of: 13.9°, 17.7°, 18.4°, 19.4°, 20.5°, 21.3°, 21.8°, 23.2°, 24.2° and 24.9°. In another further preferred embodiment of the third aspect, the PXRD diffractogram further comprises peaks, expressed in degrees 2θ (±0.2°), at 13.9°, 17.7°, 18.4°, 19.4°, 20.5°, 21.3°, 21.8°, 23.2°, 24.2° and 24.9°.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DETAILED DESCRIPTION

The present invention provides novel crystalline forms of Ibrutinib providing improved properties when compared to known crystalline forms of Ibrutinib. Depending on the specific crystalline form of the invention used, properties that differ between the invention and the known crystalline forms of Ibrutinib include: packing properties such as molar volume, density and hygroscopicity; thermodynamic properties such as melting and solubility; kinetic properties such as dissolution rate and chemical/polymorphic stability; surface properties such as crystal habit; and mechanical properties such as hardness, tensile strength, compactibility, tableting, handling, flow, and blending.

Further, the novel solvated forms of the present invention incorporate solvents found in the U.S. Food & Drug Administration's GRAS and EAFUS lists, and are stable, well-defined and controllable (i.e., the constitution of the solvates have, to date, not shown sensitivity to extrinsic factors such as atmospheric moisture or temperature). Furthermore, the crystalline forms of the present invention may be prepared by facile and industrially advantageous processes when compared to the crystalline forms of Ibrutinib known in the art. The improved properties provided by the novel crystalline forms of the present invention provide practical advantages over known forms of Ibrutinib that can be exploited to meet specific needs in the manufacture and formulation of Ibrutinib.

Depending on the manner in which the embodiments of the invention are prepared, the methodology and instrument used for PXRD analysis, and the scale selected to display results, the intensity of a given peak observed in the PXRD diffractogram may vary when compared to the same peak in the representative PXRD diffractograms provided in FIGS. 1, 2, 3 and 6 to illustrate the embodiments of the invention provided herein. Thus, differences in relative peak intensities between peaks in a PXRD diffractogram for a given crystalline form may be observed when compared to the relative peak intensities of the peaks in the representative PXRD diffractograms of FIGS. 1, 2, 3 and 6. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractograms provided in FIGS. 1, 2, 3 and 6, it is understood that individual peak positions may vary between ±0.2° 2θ from the values observed in the representative PXRD diffractograms provided in FIGS. 1, 2, 3 and 6 for the crystalline forms of the invention, or listed in Tables 1, 2, 3 and 5. Such variations are known and understood by a person of skill in the art, and any such variations do not depart from the invention disclosed herein.

Further, it is understood that, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 1, 2, 3 and 6. Thus, PXRD diffractograms of the crystalline forms of the present invention may, in some circumstances, display the same relative peak positions as observed in the representative PXRD diffractograms provided in FIGS. 1, 2, 3 and 6, with the exception that each peak is offset in the same direction, and by approximately the same amount, such that the overall PXRD diffractogram is substantially the same in appearance as a PXRD diffractogram of FIGS. 1, 2, 3 and 6, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIGS. 1, 2, 3 and 6 for the crystalline forms of the invention.

As used herein, the term 'crystalline form' refers to a substance with a particular arrangement of molecular components in its crystal lattice, and which may be identified by physical characterization methods such as PXRD. As used herein, the term crystalline form is intended to include single-component and multiple-component crystalline forms of Ibrutinib. Single-component forms of Ibrutinib consist solely of Ibrutinib in the repeating unit of the crystal lattice. Multiple-component forms of Ibrutinib include solvates of Ibrutinib wherein a solvent is also incorporated into the crystal lattice.

As used herein, the term 'solvate' refers to a multiple-component crystalline form as defined above containing both Ibrutinib and a co-former which is liquid under ambient conditions.

Multi-component crystalline forms comprising more than one type of molecule, such as solvates, may have some variability in the exact molar ratio of their components depending on a variety of conditions used. For example, a molar ratio of components within a solvate provides a person of skill in the art information as to the general relative quantities of the components of the solvate. In many cases, the molar ratio may vary by ±20% from a stated range. For example, with respect to the present invention, a molar ratio of 1:0.5 should be understood to include the ratios 1:0.4 and 1:0.6, as well as all of the individual ratios in between.

As used herein, when referring to a solvent content, the term "weight percentage" (wt %) refers to the ratio: weight solvent/(weight solvent+weight Ibrutinib), expressed as a percentage.

As used herein, the term "room temperature" refers to a temperature in the range of 20° C. to 25° C.

As used herein, the term "overnight" refers to a time of 16 to 24 hours.

Unless defined otherwise herein, the term "approximately", when used in reference to a weight percentage, allows for a variance of plus or minus 10%.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In a first embodiment of the present invention, there is provided a new crystalline form of Ibrutinib, Ibrutinib Form APO-I. Preferably, Form APO-I is unsolvated. More preferably, Form APO-I is anhydrous and unsolvated.

Ibrutinib Form APO-I can be characterized by a PXRD diffractogram comprising, among other peaks, characteristic peaks, expressed in degrees 2θ (±0.2°), at 5.1°, 7.6° and 12.5°. Preferably, the PXRD diffractogram further comprises at least three peaks, expressed in degrees 2θ (±0.2°), selected from the group consisting of: 10.1°, 11.1°, 14.2°, 15.4°, 16.3°, 17.3° and 18.7°. More preferably, the PXRD diffractogram further comprises peaks, expressed in degrees 2θ (±0.2°), at 10.1°, 11.1°, 14.2°, 15.4°, 16.3°, 17.3° and 18.7°. PXRD studies of capped and uncapped samples of Ibrutinib Form APO-I have shown that this crystal form is stable following storage in stability chambers maintained at 27° C./60% RH for at least 31 days and 40° C./75% RH for at least 21 days.

Figure 1:
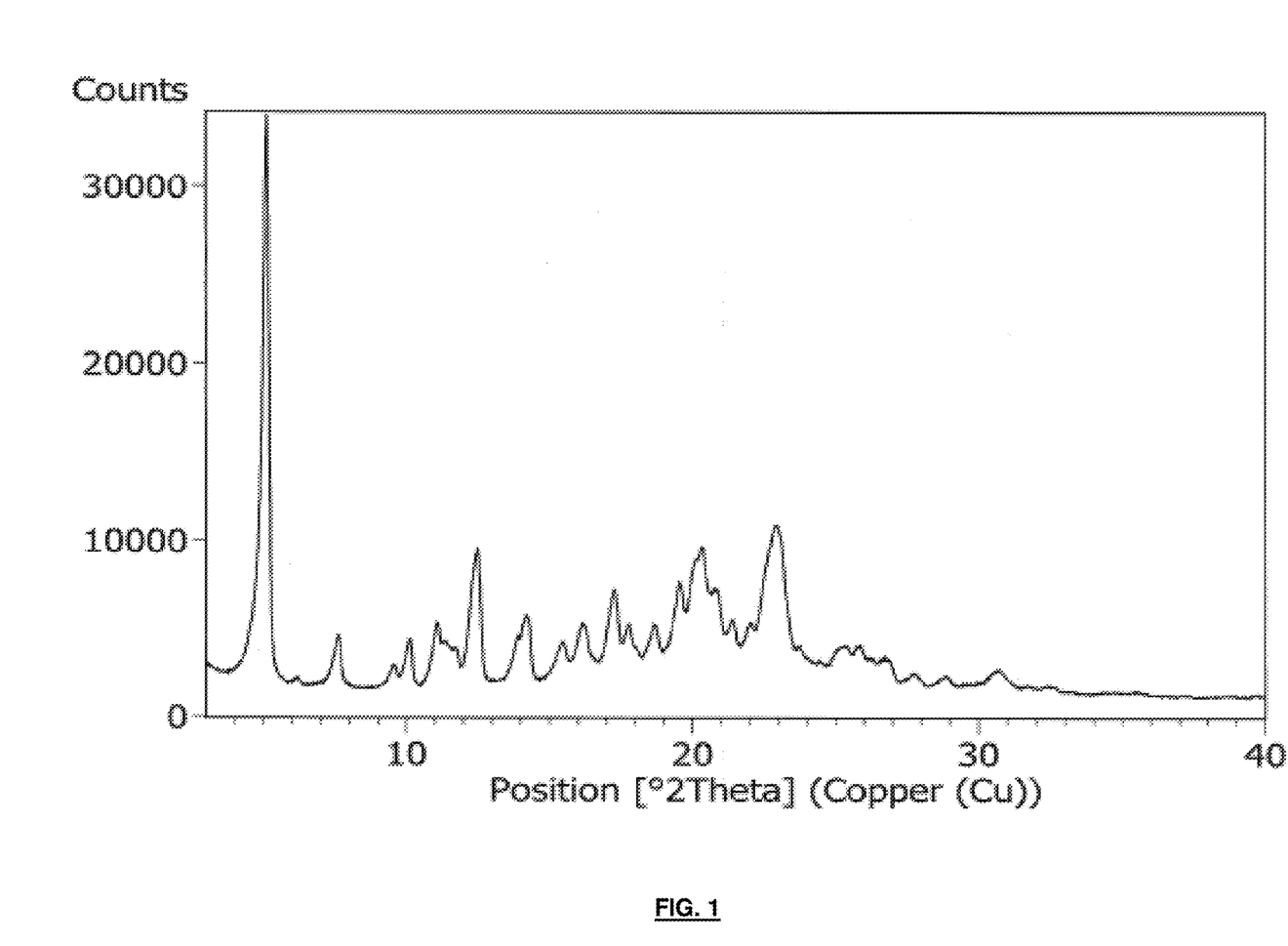
FIG. 1 is a PXRD diffractogram of Ibrutinib Form APO-I as prepared in Example 1.

A first illustrative PXRD diffractogram of Ibrutinib Form APO-I, as prepared in Example 1, is shown in FIG. 1. A peak listing, comprising peaks from the PXRD diffractogram in FIG. 1, and their relative intensities, is provided in Table 1. Although illustrative of the PXRD diffractogram that is provided for the Ibrutinib Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of Ibrutinib Form APO-I from FIG. 1

| Angle (° 2θ) | Relative intensity (%) |
|---|---|
| 5.11 | 100.00 |
| 7.60 | 9.26 |
| 10.09 | 8.79 |
| 11.05 | 7.57 |
| 12.50 | 20.70 |
| 14.20 | 10.71 |
| 15.40 | 5.08 |
| 16.26 | 2.64 |
| 17.30 | 6.92 |
| 18.65 | 6.47 |

Figure 2:
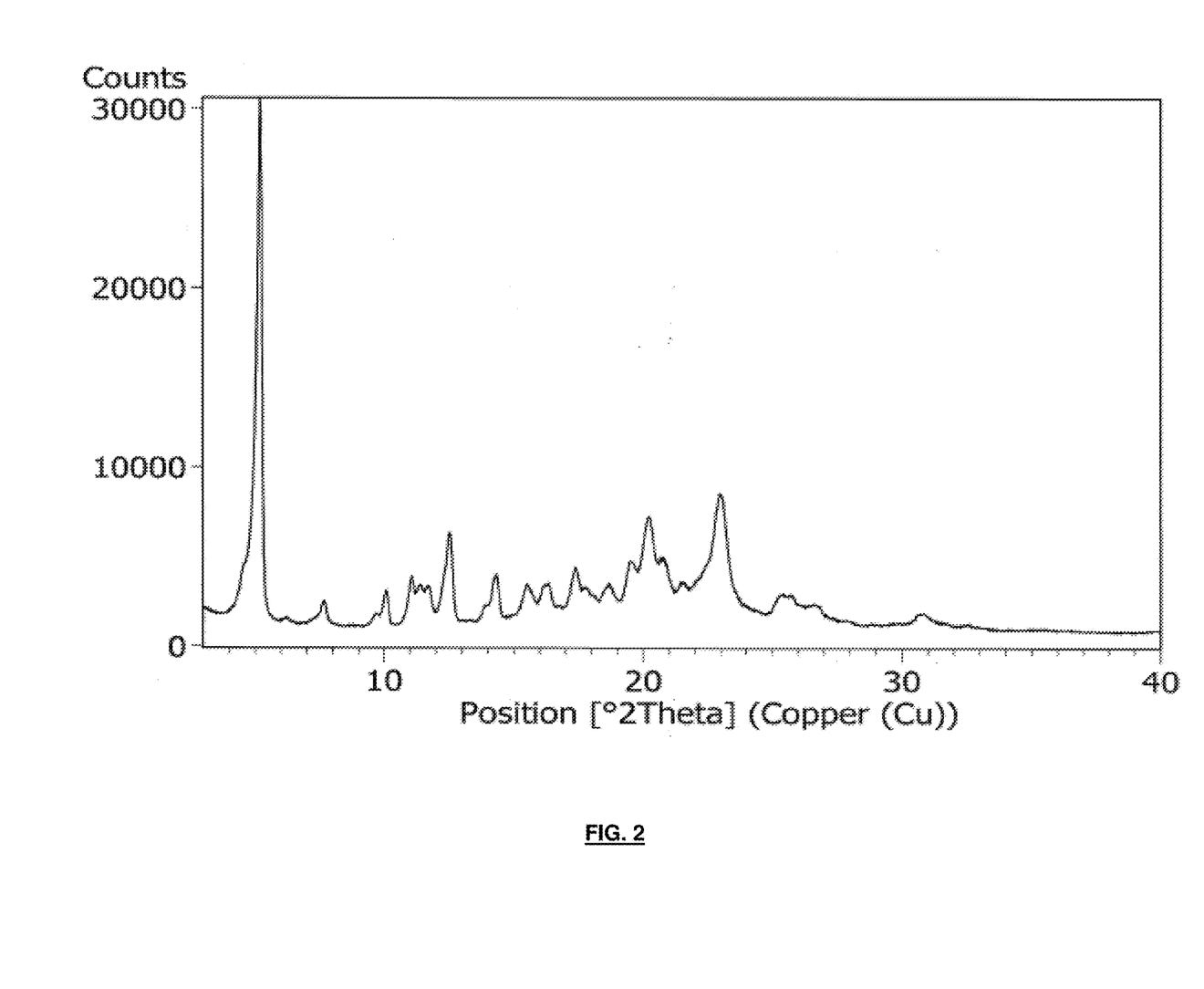
FIG. 2 is a PXRD diffractogram of Ibrutinib Form APO-I as prepared in Example 2.

A second illustrative PXRD diffractogram of Ibrutinib Form APO-I, as prepared in Example 2, which utilizes an extended drying time, is shown in FIG. 2. A peak listing, comprising peaks from the PXRD diffractogram in FIG. 2, and their relative intensities, is provided in Table 2. This illustrates how minor inter-batch variations in peak positions and peak intensities can be observed in the PXRD diffractogram for a given crystalline form. Thus, depending on a particular sample, the position and prominence or relative intensity of the peaks observed may differ from those in the illustrative PXRD diffractograms and peak listings provided.

TABLE 2

Relative peak intensities of Ibrutinib Form APO-I from FIG. 2

| Angle (° 2θ) | Relative intensity (%) |
|---|---|
| 5.18 | 100.00 |
| 7.66 | 4.69 |
| 10.07 | 6.65 |
| 11.05 | 6.45 |
| 12.48 | 16.92 |
| 14.29 | 8.31 |
| 15.51 | 4.56 |
| 16.37 | 3.35 |
| 17.37 | 6.34 |
| 18.65 | 3.32 |

As described in Examples 1 and 2, Ibrutinib Form APO-I can be prepared by the drop-wise addition of water to a heated solution of Ibrutinib in 2,2,2-trifluoroethanol while it is allowed to cool. Filtration of the resulting suspension provides Ibrutinib Form APO-I having a PXRD diffractogram consistent with that of FIG. 1 and FIG. 2.

In a second embodiment of the present invention, there is provided a second new crystalline form of Ibrutinib, Ibrutinib Form APO-II, which is a solvate of Ibrutinib and methyl benzoate. Preferably, in Ibrutinib Form APO-II, the molar ratio of Ibrutinib to methyl benzoate is approximately 1:0.5.

Ibrutinib Form APO-II can be characterized by a PXRD diffractogram comprising, among other peaks, characteristic peaks, expressed in degrees 2θ (±0.2°), at 6.4°, 10.1° and 12.8°. Preferably, the PXRD diffractogram further comprises at least three peaks, expressed in degrees 2θ (±0.2°), selected from the group consisting of: 13.8°, 17.6°, 18.4°, 19.4°, 20.4°, 21.0°, 21.7°, 23.2°, 24.1° and 24.9°. More preferably, the PXRD diffractogram further comprises peaks, expressed in degrees 2θ (±0.2°), at 13.8°, 17.6°, 18.4°, 19.4°, 20.4°, 21.0°, 21.7°, 23.2°, 24.1° and 24.9°. PXRD studies of capped and uncapped samples of Ibrutinib Form APO-II have shown that this crystal form is stable following storage in stability chambers maintained at 27° C./60% RH and 40° C./75% RH for at least 25 days.

Figure 3:
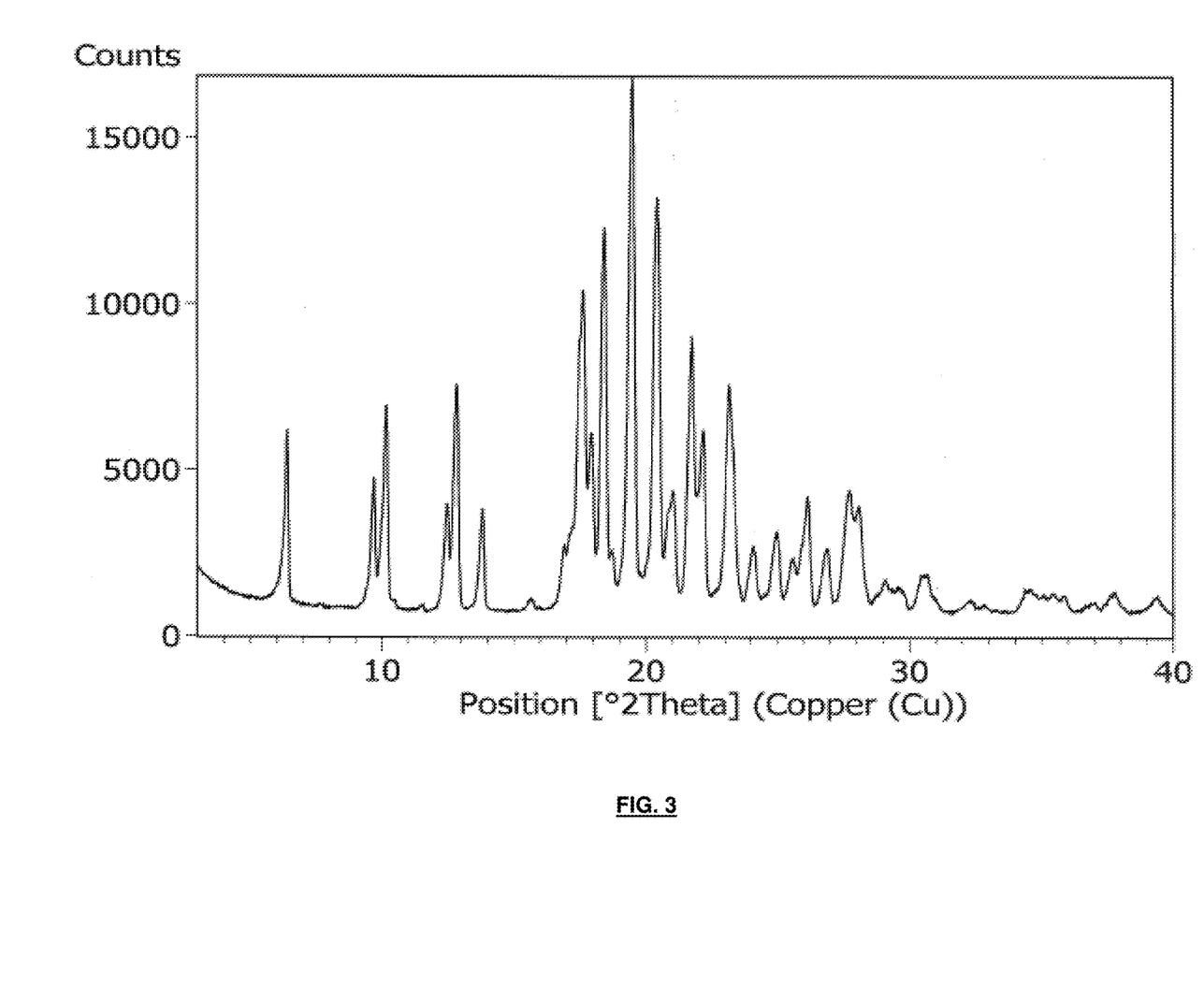
FIG. 3 is a PXRD diffractogram of Ibrutinib Form APO-II.

An illustrative PXRD diffractogram of Ibrutinib Form APO-II is shown in FIG. 3. A peak listing, comprising peaks from the PXRD diffractogram in FIG. 3, and their relative intensities, is provided in Table 3. Although illustrative of the PXRD diffractogram that is provided for the Ibrutinib Form APO-II of the present invention, the relative intensities of the peaks are variable. Thus, depending on a particular sample, the position and prominence or relative intensity of the peaks observed may differ from those in the illustrative PXRD diffractogram and peak listing.

TABLE 3

Relative peak intensities of Ibrutinib Form APO-II from FIG. 3

| Angle (° 2θ) | Relative intensity (%) |
|---|---|
| 6.37 | 40.93 |
| 9.66 | 27.93 |
| 10.14 | 46.99 |

TABLE 3-continued

Relative peak intensities of Ibrutinib Form APO-II from FIG. 3

| Angle (° 2θ) | Relative intensity (%) |
|---|---|
| 12.44 | 19.12 |
| 12.79 | 48.88 |
| 13.77 | 23.17 |
| 17.65 | 47.17 |
| 17.94 | 27.04 |
| 18.39 | 70.72 |
| 19.45 | 100.00 |
| 20.40 | 77.71 |
| 21.03 | 22.00 |
| 21.72 | 50.30 |
| 22.13 | 30.15 |
| 23.15 | 44.36 |
| 24.06 | 11.75 |
| 24.93 | 16.96 |

As described in Example 3, Ibrutinib Form APO-II can be prepared from a solution of Ibrutinib in methyl benzoate by heating the solution to approximately 100° C., allowing the solution to cool and then adding excess heptane anti-solvent drop-wise, during which time crystallization occurs. Filtration and drying of the resulting material provides Ibrutinib Form APO-II having a PXRD diffractogram consistent with that of FIG. 3.

Figure 4:
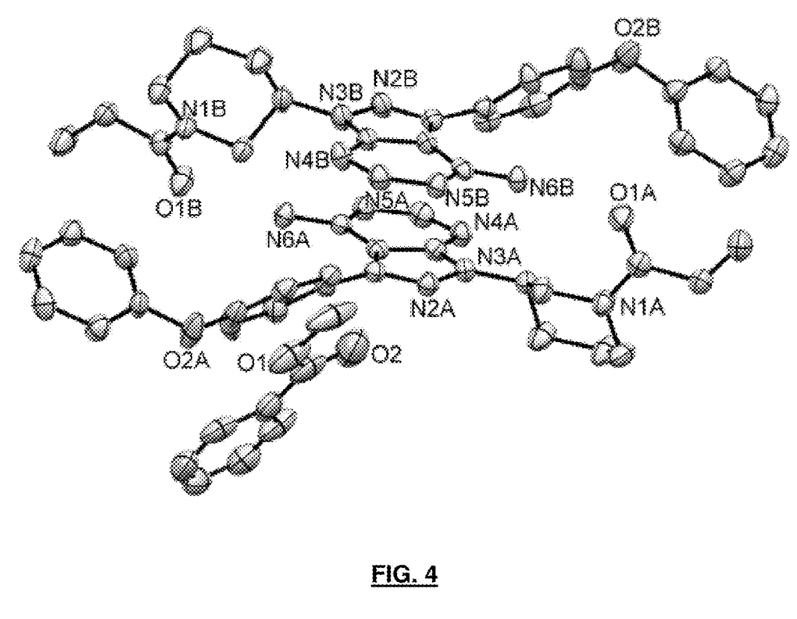
FIG. 4 is an Oak Ridge Thermal Ellipsoid Plot (ORTEP) illustration of the SCXRD of Form APO-II.

Single crystals of Ibrutinib were grown from a layered solution of methyl benzoate and heptanes as described in Example 4, and characterized by SCXRD. A summary of the SCXRD data is provided in Table 4. An ORTEP illustration of the unit cell from the SCXRD structure is shown in FIG. 4. This illustration depicts a 2:1 Ibrutinib:methyl benzoate solvate, i.e., the molar ratio of Ibrutinib to methyl benzoate is 1:0.5.

TABLE 4

Single Crystal X-Ray Diffraction Parameters of the 2:1 Ibrutinib:methyl benzoate solvate (Form APO-II)

| Formula | $C_{25}H_{24}N_6O_2 \cdot \frac{1}{2}C_8H_8O_2$ |
|---|---|
| Formula Weight (g/mol) | 508.57 |
| Crystal System | triclinic |
| Space Group | P1 |
| Temperature, K | 110 |
| a, Å | 10.1282(16) |
| b, Å | 10.2383(16) |
| c, Å | 14.246(3) |
| α, ° | 95.523(7) |
| β, ° | 102.506(5) |
| γ, ° | 115.706(4) |
| V, Å$^3$ | 1268.8(4) |
| Z | 2 |
| ρ (g/cm) | 1.331 |
| λ, Å, (CuKα) | 1.54178 |
| Measured fraction of data | 0.969 |
| Unique reflections measured/ reflections included in refinement | 6961 |
| $R_1$ | 0.0453 |
| $wR_2$ | 0.1159 |
| $R_1$ (all data) | 0.0489 |
| $wR_2$ (all data) | 0.1194 |
| Goodness of Fit | 1.037 |
| Min & Max peak heights on final ΔF Map (e$^-$/Å) | −0.276, 0.590 |

Figure 5:
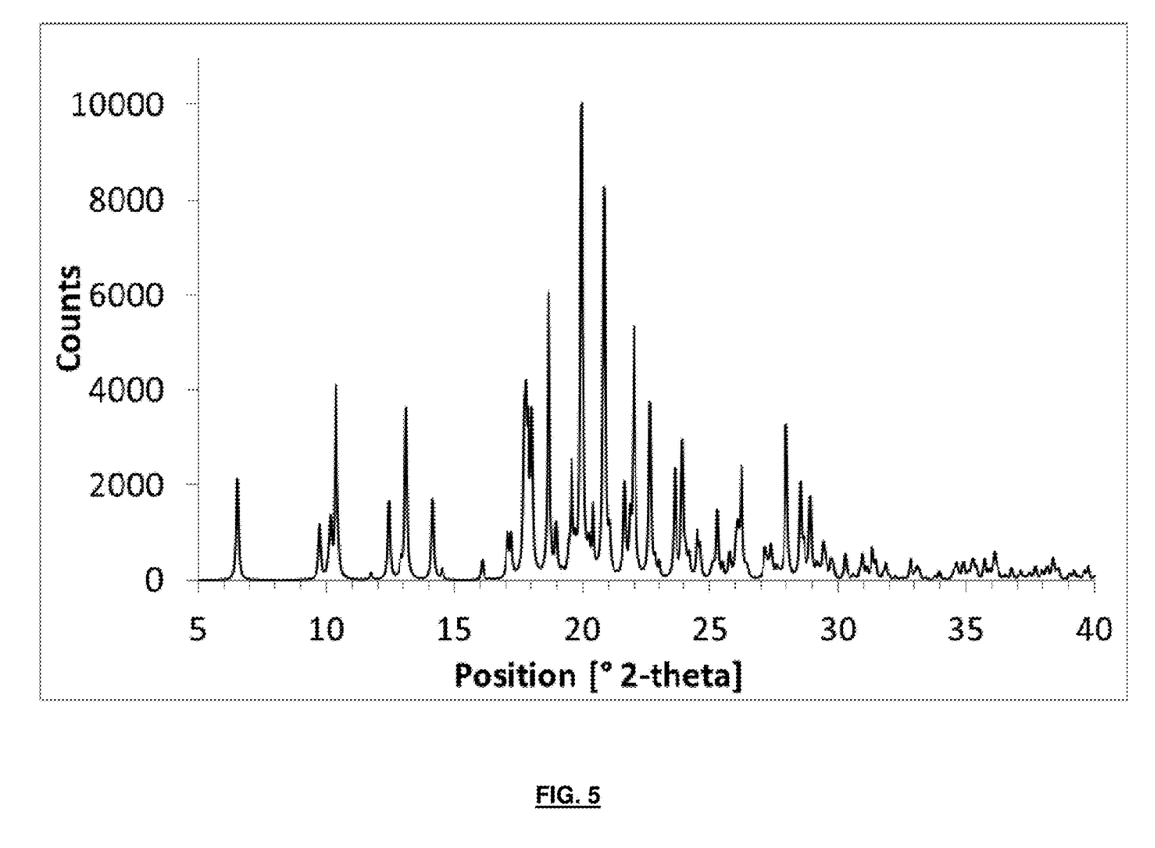
FIG. 5 is a calculated PXRD diffractogram of Form APO-II based on Single Crystal X-Ray Diffraction (SCXRD).

A calculated PXRD diffractogram based on the SCXRD data is shown in FIG. 5. This calculated PXRD diffractogram shows that the single crystal analyzed provides a PXRD pattern that is consistent with the PXRD diffractogram provided by Ibrutinib Form APO-II.

In a third embodiment of the present invention, there is provided a third new crystalline form of Ibrutinib, Ibrutinib Form APO-IV, a solvate of Ibrutinib and methyl salicylate. Preferably, in Ibrutinib Form APO-IV, the molar ratio of Ibrutinib to methyl salicylate is approximately 1:0.5.

Ibrutinib Form APO-IV can be characterized by a PXRD diffractogram comprising, among other peaks, characteristic peaks, expressed in degrees 2θ (±0.2°), at 6.4°, 10.2° and 12.9°. Preferably, the PXRD diffractogram further comprises at least three peaks, expressed in degrees 2θ (±0.2°), selected from the group consisting of: 13.9°, 17.7°, 18.4°, 19.4°, 20.5°, 21.3°, 21.8°, 23.2°, 24.2° and 24.9°. More preferably, the PXRD diffractogram further comprises peaks, expressed in degrees 2θ (±0.2°), at 13.9°, 17.7°, 18.4°, 19.4°, 20.5°, 21.3°, 21.8°, 23.2°, 24.2° and 24.9°. PXRD studies of uncapped samples of Ibrutinib Form APO-IV have shown that this crystal form is stable following storage in a stability chambers maintained at 40° C./75% RH for at least 11 months.

Figure 6:
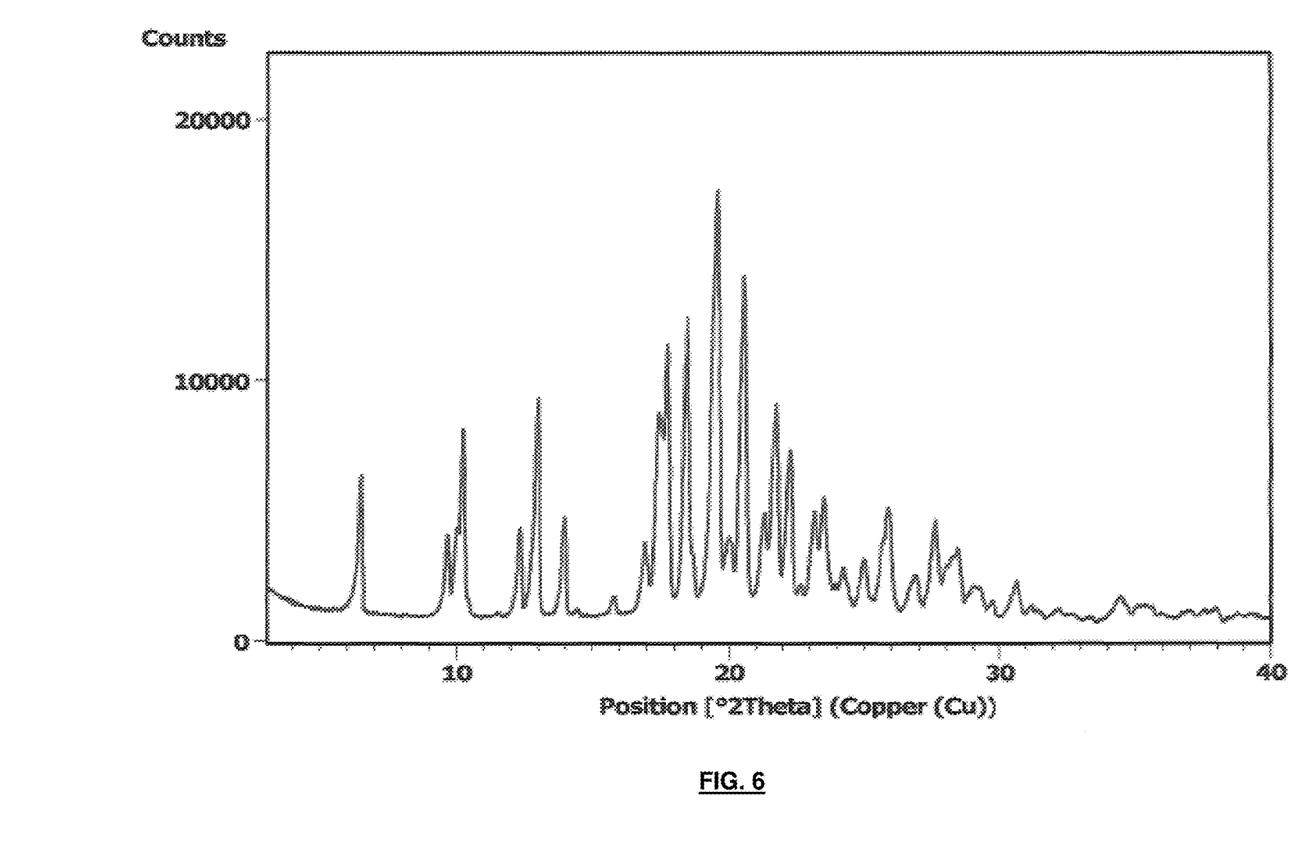
FIG. 6 is a PXRD diffractogram of Ibrutinib Form APO-IV.

An illustrative PXRD diffractogram of Ibrutinib Form APO-IV is shown in FIG. 6. A peak listing, comprising peaks from the PXRD diffractogram in FIG. 6, and their relative intensities, is provided in Table 5. Although illustrative of the PXRD diffractogram that is provided for the Ibrutinib Form APO-IV of the present invention, the relative intensities of the peaks are variable. Thus, depending on a particular sample, the position and prominence or relative intensity of the peaks observed may differ from those in the illustrative PXRD diffractogram and peak listing.

TABLE 5

Relative peak intensities of Ibrutinib Form APO-IV from FIG. 6

| Angle (° 2θ) | Relative intensity (%) |
|---|---|
| 6.45 | 31.36 |
| 9.63 | 15.52 |
| 10.22 | 44.46 |
| 12.29 | 20.84 |
| 12.92 | 48.01 |
| 13.92 | 23.64 |
| 17.46 | 37.75 |
| 17.74 | 59.99 |
| 18.44 | 66.29 |
| 19.58 | 100.00 |
| 20.51 | 79.27 |
| 21.27 | 14.28 |
| 21.63 | 32.82 |
| 22.21 | 36.02 |
| 23.11 | 13.64 |
| 24.23 | 6.11 |
| 24.95 | 10.51 |

As described in Example 5, Ibrutinib Form APO-IV can be prepared from a solution of Ibrutinib in methyl salicylate by heating the solution to approximately 100° C., allowing the solution to cool, and then adding excess heptane anti-solvent drop-wise, during which time crystallization occurs. Filtration and drying of the resulting material provides Ibrutinib Form APO-IV having a PXRD diffractogram consistent with that of FIG. 6.

Figure 7:
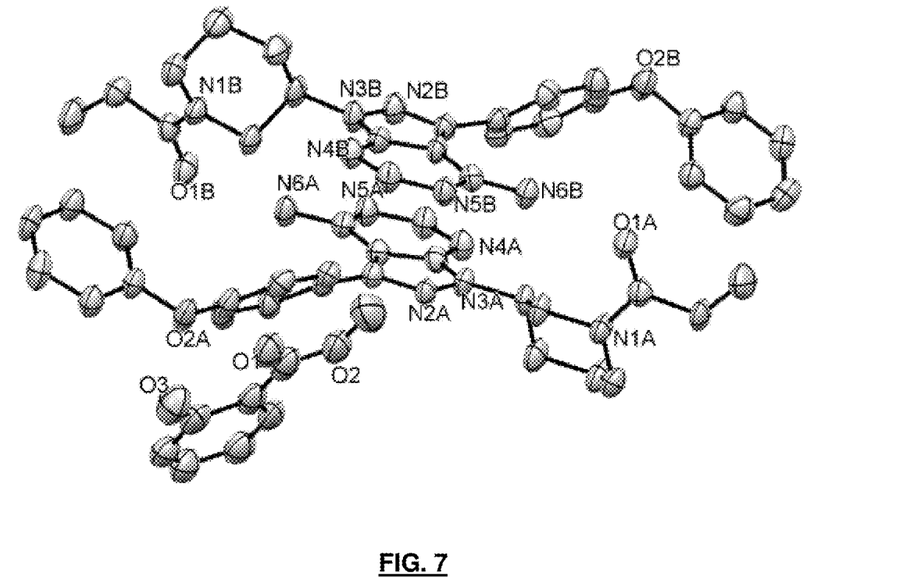
FIG. 7 is an ORTEP illustration of the SCXRD of Form APO-IV.

Single crystals of Ibrutinib were grown from a layered solution of Ibrutinib in methyl salicylate and heptane as described in Example 6, and characterized by SCXRD. A summary of the SCXRD data is provided in Table 6. An ORTEP illustration of the unit cell from the SCXRD structure is shown in FIG. 7. This illustration depicts a 2:1 Ibrutinib:methyl salicylate solvate, i.e., the molar ratio of Ibrutinib to methyl salicylate is 1:0.5.

TABLE 6

Single Crystal X-Ray Diffraction Parameters of the 2:1
Ibrutinib:methyl salicylate solvate (Form APO-IV)

| Formula | $C_{25}H_{24}N_6O_2 \cdot \frac{1}{2}C_8H_8O_3$ |
|---|---|
| Formula Weight (g/mol) | 516.57 |
| Crystal System | triclinic |
| Space Group | P 1 |
| Temperature, K | 110 |
| a, Å | 10.172(2) |
| b, Å | 10.354(2) |
| c, Å | 14.125(3) |
| α, ° | 96.053(11) |
| β, ° | 101.675(13) |
| γ, ° | 116.200(10) |
| V, Å$^3$ | 1274.6(5) |
| Z | 2 |
| ρ (g/cm) | 1.346 |
| λ, Å, (CuKα) | 1.54178 |
| Measured fraction of data | 0.969 |
| Unique reflections measured | 6218 |
| R$_1$ | 0.0659 |
| wR$_2$ | 0.1682 |
| R$_1$ (all data) | 0.0882 |
| wR$_2$ (all data) | 0.1935 |
| Goodness of Fit | 1.027 |
| Min & Max peak heights on final ΔF Map (e$^-$/Å) | −0.285, 0.439 |

Figure 8:
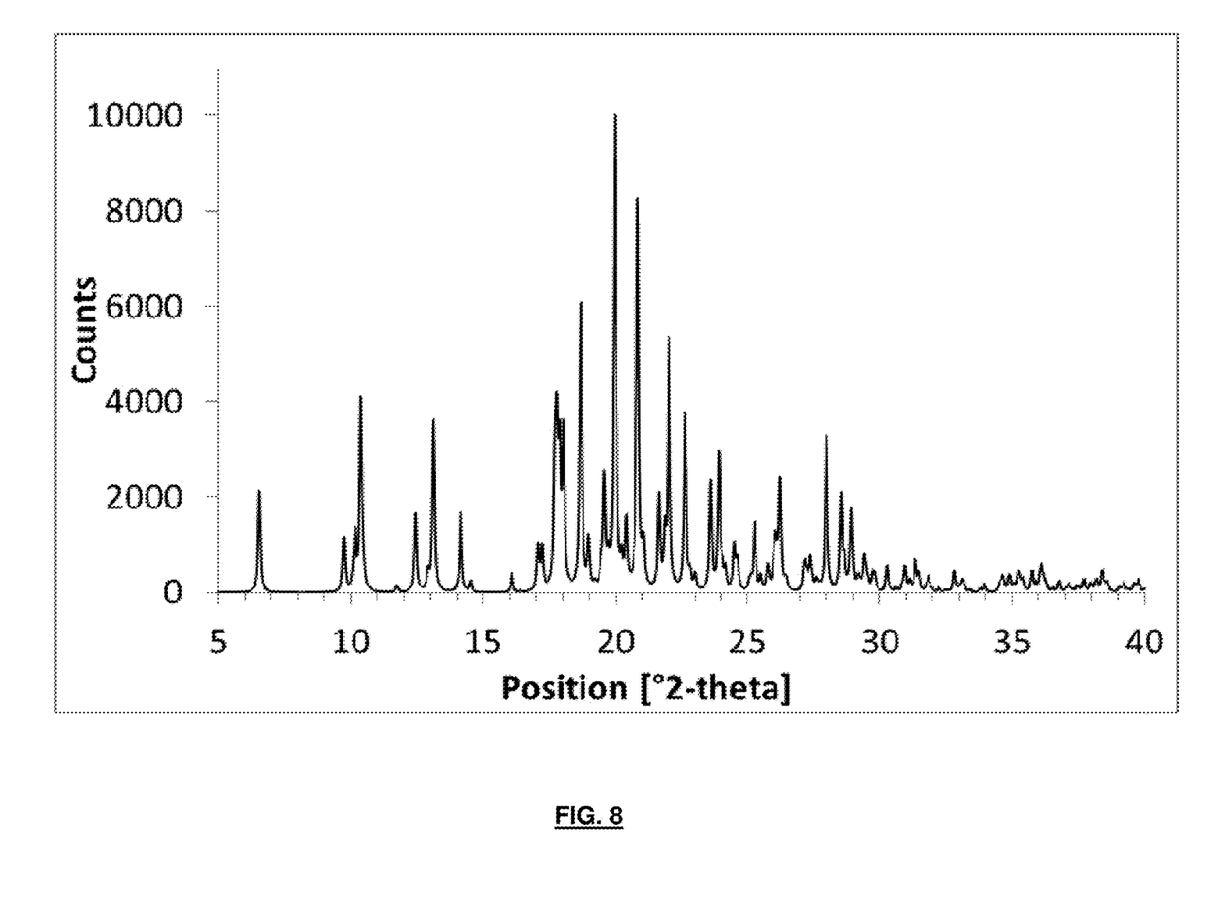
FIG. 8 is a calculated PXRD diffractogram of Form APO-IV based on SCXRD.

A calculated PXRD diffractogram based on the SCXRD data is shown in FIG. 8. This calculated PXRD diffractogram shows that the single crystal analyzed provides a PXRD pattern that is consistent with the PXRD diffractogram provided by Ibrutinib Form APO-IV.

EXAMPLES

The following non-limiting examples are illustrative of some of the aspects and embodiments of the invention described herein.

The Ibrutinib used as a starting material in the following examples was consistent with that of Ibrutinib Form A, which is reported in WO 2013/184572 A1. Other polymorphic forms are equally suitable as starting material when preparing the novel crystalline forms of Ibrutinib of the present invention.

Powder X-Ray Diffraction Analysis:

Data were acquired on a PANanalytical X-Pert Pro MPD diffractometer with fixed divergence slits and an X'Celerator RTMS detector. The diffractometer was configured in Bragg-Brentano geometry; data was collected over a 2-theta range of 3° to 40° using CuKα radiation at a power of 40 mA and 45 kV. CuKβ radiation was removed using a divergent beam nickel filter. A step size of 0.017° was used. Samples were rotated to reduce preferred orientation effects. Samples were lightly ground prior to analysis.

Single Crystal Data Collection and Processing

Samples for SCXRD analysis were mounted on a Mitegen polyimide micromount with a small amount of Paratone N oil. All X-ray measurements were made on a Bruker-Nonius KappaCCD Apex2 diffractometer at a temperature of 110 K. In the case of Form APO-II, the unit cell dimensions were determined from a symmetry constrained fit of 9826 reflections with 6.5°<2q<130.42° and the data collection strategy was a number of w and j scans which collected data up to 132.544° (2q). In the case of Form APO-IV, the unit cell dimensions were determined from a symmetry constrained fit of 4980 reflections with 6.56°<2θ<128.88° and the data collection strategy was a number of ω and φ scans which collected data up to 132.158° (2θ). Frame integration was performed using SAINT (Bruker-AXS, SAINT Version 2013.8, 2013). The resulting raw data was scaled and absorption corrected using a multi-scan averaging of symmetry equivalent data using SADABS (Bruker-AXS, SADABS Version 2012.1, 2012).

Single Crystal Structure Solution and Refinement

Single crystal structures were solved by using a dual space methodology with the SHELXT program (Sheldrick, G. M., Acta Cryst. 2015, A71, 3-8). All non-hydrogen atoms were obtained from the initial solution, with hydrogen atoms being introduced at idealized positions and allowed to ride on the parent atom. The structural model was fit to the data using full matrix least-squares based on F2. Calculated structure factors include corrections for anomalous dispersion from the usual tabulation. The absolute configuration was determined by the calculation of Parsons quotients (Parsons, S.; Flack, H. D. and Wagner, T. Acta Cryst. 2013, B69, 249-259). Structure refinement was conducted using the SHELXL-2014 program from the SHELX suite of crystallographic software (Sheldrick, G. M., Acta Cryst. 2015, C71, 3-8). Graphic plots were produced using the NRCVAX program suite (Gabe, E. J.; Le Page, Y.; Charland, J. P.; Lee, F. L. and White, P. S. J. Appl. Cryst. 1989, 22, 384-387).

Calculated PXRD Diffractograms

PXRD diffractograms were calculated from SCXRD data using the Mercury software package (CCDC, version 3.9) with λ=1.54056 as the source.

Example 1: Preparation of Ibrutinib Form APO-I

A magnetically stirred suspension of Ibrutinib (500 mg) in 2,2,2-trifluroethanol (5 mL) was warmed to 50° C. for approximately 1 hour to afford a solution. The solution was removed from the heat source and water (40 mL) was added drop-wise over one hour over which time the mixture turned to a milky suspension. After stirring overnight, the solid was collected by filtration and washed with water (5 mL) to afford Ibrutinib Form APO-I as a white solid (420 mg, 84% yield). The PXRD diffractogram of a sample prepared by this method is shown in FIG. 1.

Example 2: Preparation of Ibrutinib Form APO-I

A magnetically stirred suspension of Ibrutinib (500 mg) in 2,2,2-trifluroethanol (5 mL) was warmed to 50° C. for approximately 1 hour to afford a solution. The solution was removed from the heat source and water (40 mL) was added drop-wise over one hour over which time the mixture turned to a milky suspension. After stirring overnight, the solid was collected by filtration and washed with water (4 mL). Drying overnight under high vacuum at room temperature afforded Ibrutinib Form APO-I as a white solid (400 mg, 80% yield). The PXRD diffractogram of a sample prepared by this method is shown in FIG. 2.

Example 3: Preparation of Ibrutinib Form APO-II

A stirred suspension of Ibrutinib (400 mg) in methyl benzoate (10 mL) was heated to 100° C. for approximately 1 hour to afford a solution. The solution was allowed to cool to room temperature prior to drop-wise addition of heptane (50 mL) over approximately 1 hour. The resulting turbid suspension was stirred overnight. The solid was collected by filtration, washed with heptane (10 mL) and dried under high vacuum at room temperature to afford Ibrutinib Form APO- II as a white solid (400 mg, 78% yield). The PXRD diffractogram of a sample prepared by this method is shown in FIG. 3.

$^1$H-NMR (d$_6$-DMSO) δ=8.26 (s, 1H), 7.97 (d, J=8.5 Hz, 1H), 7.62-7.72 (m, 2.5H), 7.53 (t, J=7.5 Hz, 1H), 7.44 (t, J=7.9 Hz, 2H), 7.09-7.24 (m, 5H), 6.66-6.95 (m, 1H), 6.10 (t, J=17.9 Hz, 1H), 5.71 (d, J=9.9 Hz, 0.5H), 5.59 (d, J=11.2 Hz, 0.5H), 4.61-4.80 (m, 1H), 4.56 (d, J=12.3 Hz, 0.5H), 4.15-4.28 (br m, 1H), 4.08 (d, J=12.8 Hz, 0.5H), 3.86 (s, 1.5H) 3.62-3.80 (m, 0.5H), 3.07-3.15 (m, 1H), 3.01 (br t, J=12.1 Hz, 0.5H), 2.19-2.36 (m, 1H), 2.06-2.19 (m, 1H), 1.87-2.00 (m, 1H), 1.47-1.70 (m, 1H).

Example 4: Preparation of Single Crystals of Ibrutinib Form APO-II

A stirred suspension of Ibrutinib (100 mg) in methyl benzoate (4 mL) was heated to 100° C. for approximately 2 hours to afford a clear solution, with a clarification filtration being performed before cooling the solution to room temperature. To the cooled solution was slowly layered heptane (15 mL). The flask was left undisturbed at room temperature for several days, with crystal growth beginning after one day. Crystals were collected after gently decanting off the solvent, with one crystal being selected for SCXRD analysis. FIG. 4 depicts an ORTEP illustration of the SCXRD of the Form APO-II crystals prepared by this method. FIG. 5 depicts a calculated PXRD based on the SCXRD of this sample acquired according to the conditions given above.

Example 5: Preparation of Ibrutinib Form APO-IV

A stirred suspension of Ibrutinib (413 mg) in methyl salicylate (8 mL) was heated to 100° C. for approximately 1 hour to afford a clear solution, which was then clarified by filtration before being cooled to room temperature. Heptane (80 mL) was added to the solution drop-wise over approximately 2.5 hours. The resulting turbid suspension was stirred overnight, and the solid was collected by filtration, washed with heptane (2×10 mL), and dried under high vacuum at room temperature to afford Ibrutinib Form APO-IV as a white solid (438 mg, 90% yield). The PXRD diffractogram of a sample prepared by this method is shown in FIG. 6.

$^1$H-NMR (d$_6$-DMSO) δ=10.50 (s, 0.5H), 8.26 (s, 1H), 7.79 (dd, 0.5H), 7.65 (d, 2H), 7.53 (t, 0.5H), 7.44 (t, 2H), 7.09-7.24 (m, 5H), 6.66-6.99 (m, 1H), 6.83 (m, 05H), 6.72 (m, 0.5), 6.10 (t, 1H), 5.71 (d, 0.5H), 5.60 (d, 0.5H), 4.61-4.80 (m, 1H), 4.56 (d, 0.5H), 4.15-4.28 (m, 1H), 4.08 (d, 0.5H), 3.89 (s, 1.5H) 3.62-3.80 (m, 0.5H), 3.07-3.25 (m, 1H), 3.01 (br t, 0.5H), 2.19-2.36 (m, 1H), 2.06-2.19 (m, 1H), 1.87-2.00 (m, 1H), 1.47-1.70 (m, 1H).

Example 6: Preparation of Single Crystals of Ibrutinib Form APO-IV

A stirred suspension of Ibrutinib (36 mg) in methyl salicylate (2 mL) was heated to 100° C. for approximately 2 hours to afford a clear solution, which was then subjected to a clarification filtration before being cooled to room temperature. To the cooled solution was slowly layered heptane (10 mL). The flask was left undisturbed at room temperature for several days. Single crystal growth began after 1 day. Crystals were collected after gently decanting off the solvent, with one crystal being selected for SCXRD analysis. FIG. 7 depicts an ORTEP illustration of the SCXRD of the Form APO-II crystals prepared by this method. FIG. 8 depicts a calculated PXRD based on the SCXRD of this sample acquired according to the conditions given above.

What is claimed is:

1. A crystalline form of Ibrutinib that is a solvate of Ibrutinib and methyl benzoate.
2. The solvate of claim 1, wherein the molar ratio of Ibrutinib to methyl benzoate is approximately 1:0.5.
3. The solvate of claim 2, wherein the solvate is characterized by a powder X-ray diffraction (PXRD) diffractogram comprising peaks, expressed in degrees 2θ (±0.2°), at 6.4°, 10.1° and 12.8°.
4. The solvate of claim 3, characterized by a PXRD diffractogram further comprising at least three peaks, expressed in degrees 2θ (±0.2°), selected from the group consisting of: 13.8°, 17.6°, 18.4°, 19.4°, 20.4°, 21.0°, 21.7°, 23.2°, 24.1° and 24.9°.
5. The solvate of claim 3, characterized by a PXRD diffractogram further comprising peaks, expressed in degrees 2θ (±0.2°), at 13.8°, 17.6°, 18.4°, 19.4°, 20.4°, 21.0°, 21.7°, 23.2°, 24.1° and 24.9°.

* * * * *